United States Patent
Ichiura et al.

(10) Patent No.: US 8,440,731 B2
(45) Date of Patent: May 14, 2013

(54) METHOD FOR PRODUCING FUNCTIONAL MATERIAL, FUNCTIONAL MATERIAL, SHEET-LIKE STRUCTURE AND SANITARY PRODUCT

(75) Inventors: Hideaki Ichiura, Kanonji (JP); Masaaki Morikawa, Kanonji (JP); Masaki Takahashi, Kanonji (JP); Noriyoshi Nishida, Kanonji (JP); Takamitsu Igaue, Kanonji (JP); Takayoshi Konishi, Kanonji (JP)

(73) Assignee: Unicharm Corporation, Ehime (JP)

( * ) Notice: Subject to any disclaimer, the term of this patent is extended or adjusted under 35 U.S.C. 154(b) by 608 days.

(21) Appl. No.: 12/449,087

(22) PCT Filed: Jan. 22, 2008

(86) PCT No.: PCT/JP2008/050822
§ 371 (c)(1),
(2), (4) Date: Feb. 2, 2010

(87) PCT Pub. No.: WO2008/090892
PCT Pub. Date: Jul. 31, 2008

(65) Prior Publication Data
US 2010/0144909 A1 Jun. 10, 2010

(30) Foreign Application Priority Data
Jan. 22, 2007 (JP) ................ P2007-011969

(51) Int. Cl.
*B01J 39/20* (2006.01)
(52) U.S. Cl.
USPC ................ 521/38; 424/484; 424/499

(58) Field of Classification Search ............. 521/38; 424/499, 484
See application file for complete search history.

(56) References Cited

U.S. PATENT DOCUMENTS

| | | | | |
|---|---|---|---|---|
| 5,700,397 | A * | 12/1997 | Maeda et al. | 428/402.24 |
| 6,638,917 | B1 | 10/2003 | Li et al. | |
| 6,656,508 | B2 * | 12/2003 | Goldenberg et al. | 424/499 |
| 6,693,089 | B1 * | 2/2004 | Li et al. | 514/54 |

(Continued)

FOREIGN PATENT DOCUMENTS

| | | |
|---|---|---|
| CN | 1187289 A | 7/1998 |
| JP | 02-274258 | * 11/1990 |

(Continued)

OTHER PUBLICATIONS

Chinese Office Action from corresponding Chinese application No. 2008800028298 and English translation dated May 29, 2012 (10 pgs).

(Continued)

*Primary Examiner* — Peter D. Mulcahy
*Assistant Examiner* — Henry Hu
(74) *Attorney, Agent, or Firm* — Brinks Hofer Gilson & Lione

(57) ABSTRACT

Provided is a method for producing a functional material, including the steps of: bringing a polyvalent metal cation aqueous solution into contact with a base material; bringing a polyanion aqueous solution containing a functional component into contact with the base material previously in contact with the polyvalent metal cation aqueous solution to bond the polyvalent metal cations and the polyanions to each other, and thereby forming an insoluble compound containing the functional component; and drying the base material including the insoluble compound.

3 Claims, 4 Drawing Sheets

U.S. PATENT DOCUMENTS

| | | | |
|---|---|---|---|
| 6,726,934 B1 * | 4/2004 | Prokop | 424/500 |
| 2002/0001619 A1 * | 1/2002 | Goldenberg et al. | 424/484 |
| 2004/0136961 A1 * | 7/2004 | Prokop et al. | 424/93.2 |
| 2007/0001156 A1 * | 1/2007 | Toreki, III | 252/601 |
| 2007/0092625 A1 * | 4/2007 | Ishimoto et al. | 426/598 |

FOREIGN PATENT DOCUMENTS

| | | | |
|---|---|---|---|
| JP | 2940930 | | 11/1990 |
| JP | 02-311534 | * | 12/1990 |
| JP | 02-311535 | * | 12/1990 |
| JP | 02-311536 | * | 12/1990 |
| JP | 2728298 | | 12/1990 |
| JP | 2728299 | | 12/1990 |
| JP | 2862275 | | 12/1990 |
| JP | 2001-524084 A | * | 11/2001 |
| WO | WO 98/46211 | | 10/1998 |

OTHER PUBLICATIONS

Chinese Office Action from corresponding Chinese application No. 200880002829.8 dated Dec. 17, 2012 (6 pgs).

* cited by examiner

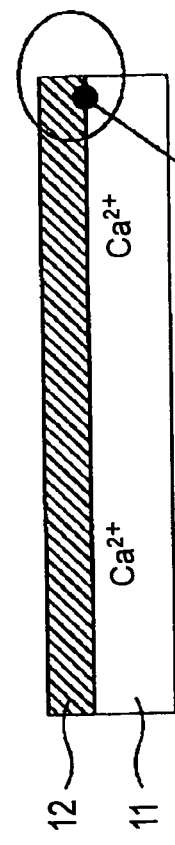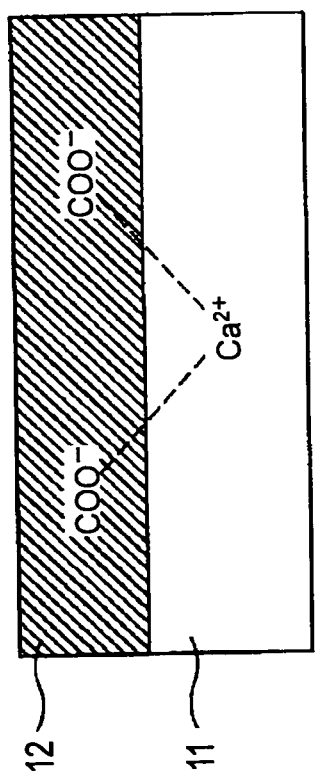
FIG. 1(A)
FIG. 1(B)

METHOD FOR PRODUCING FUNCTIONAL MATERIAL, FUNCTIONAL MATERIAL, SHEET-LIKE STRUCTURE AND SANITARY PRODUCT

RELATED APPLICATIONS

The present application is a 35 U.S.C. §371 national stage filing of International Patent Application No. PCT/JP2008/050822, filed Jan. 22, 2008, to which priority is claimed under 35 U.S.C. §120 and through which priority is claimed under 35 U.S.C. §119 to Japanese Priority Patent Application No. 2007-011969, filed Jan. 22, 2007.

TECHNICAL FIELD

The present invention relates to: a functional material which contains a functional component such as a moisture retention component, an antibacterial component, a moisture absorbing component, a deodorizing component, an aroma component or an anti-inflammatory component and which releases the functional component; a sheet-like structure using the functional material; and a method for producing the functional material. Further, the present invention relates to sanitary products using the sheet-like structure, and more specifically to sanitary products used as: an absorbent product such as a disposable diaper, a sanitary napkin, a panty liner and a urine pad; a wound protection sheet; and a wipe for human body.

BACKGROUND ART

In recent years, intelligent materials have been attracting attention. An intelligent material refers to a material which exhibits its function in response to an external stimulus such as temperature, pH, or body fluid. Typical intelligent materials are exemplified by a drug delivery system, a self healing material and the like.

In order to provide an intelligent function to a sheet-like structure such as a nonwoven fabric, there are effective methods, for example, a method of applying porous microcapsules having a functional component encapsulated therein, and a method of pasting a film containing a functional component. Provided with an intelligent function responsive to an external stimulus, a sheet-like structure can be a functional material which is capable of exhibiting its maximum function when needed and of protecting the functional component until being used.

At present, an integration of an intelligent material and a sheet-like structure is generally performed by a coating method using a binder. However, with the coating method using a binder, the binder covers the surfaces of the microcapsules and the film, so that the intelligent material loses a function responsive to an external stimulus, the function being unique to the intelligent material. Therefore, the coating method using a binder is not suitable for the integration of a functional material containing a functional component and a sheet-like structure such as a nonwoven fabric.

Here, Japanese Patent No. 2728298 (Patent Document 1), Japanese Patent No. 2728299 (Patent Document 2), Japanese Patent No. 2862275 (Patent Document 3), and Japanese Patent No. 2940930 (Patent Document 4) describe methods for producing a hydrated alginic acid film by utilizing such a property of a soluble alginate that the soluble alginate can easily be gelatinized by reaction thereof in an aqueous solution with a divalent metal salt such as a salt containing calcium ion. The hydrated alginic acid film can be applied to external preparations such as medicines, and cosmetics, and is capable of containing an appropriate functional component such as a moisture retention agent, a sanitizer or the like, in accordance its application.

However, the film obtained by any of the methods described in the foregoing Patent Documents 1 to 4 is a hydrated film. Accordingly, when used as a sanitary product, which is used in constant contact with a skin, the film releases the functional component by simply being applied with an external pressure without being in contact with a body fluid such as sweat. Thus, it is impossible to render the release of the functional component body-fluid responsive.

DISCLOSURE OF THE INVENTION

The present invention has solved the above-described conventional problems, and an object of the present invention is to provide: a method for producing a functional material having excellent body-fluid responsiveness; a functional material; a sheet-like structure; and a sanitary product.

The present inventors have found out that the body-fluid responsiveness can remarkably be improved by bringing a polyanion aqueous solution containing a functional component into contact with a base material coated with a polyvalent metal salt aqueous solution and then drying the resulting base material, resulting in completion of the present invention.

Specifically, a first aspect of the present invention provides a method for producing a functional material, including the steps of: bringing a polyvalent metal cation aqueous solution into contact with a base material; bringing a polyanion aqueous solution containing a functional component into contact with the base material previously in contact with the polyvalent metal cation aqueous solution to bond the polyvalent metal cations and the polyanions to each other, and thereby forming an insoluble compound containing the functional component; and drying the base material including the insoluble compound.

A second aspect of the present invention provides a method for producing a functional material, including the steps of: bringing a polyanion aqueous solution containing a functional component into contact with a base material; bringing a polyvalent metal cation aqueous solution into contact with the base material previously in contact with the polyanion aqueous solution to bond the polyvalent metal cations and the polyanions to each other, and thereby forming an insoluble compound containing the functional component; and drying the base material including the insoluble compound.

A third aspect of the present invention provides a functional material produced by drying a base material including an insoluble compound containing a functional component, the insoluble compound being formed by bringing a polyanion aqueous solution containing the functional component into contact with the base material including a polyvalent metal cation aqueous solution, to bond the polyvalent metal cations and the polyanions to each other.

A fourth aspect of the present invention provides a functional material produced by drying a base material including an insoluble compound containing a functional component, the insoluble compound being formed by bringing a polyvalent metal cation aqueous solution into contact with the base material including a polyanion aqueous solution containing the functional component to thereby bond the polyvalent metal cations and the polyanions to each other.

A fifth aspect of the present invention provides a sheet-like structure including the above-described functional material according to the present invention.

Furthermore, a fifth aspect of the present invention provides a sanitary product using the above-described functional material according to the present invention.

BRIEF DESCRIPTION OF THE DRAWINGS

FIG. 1 is a schematic diagram showing a cross-section of a calcium alginate gel film formed by a cross linking reaction between sodium alginate and calcium ions.

BEST MODES FOR CARRYING OUT THE INVENTION

Figure 2:
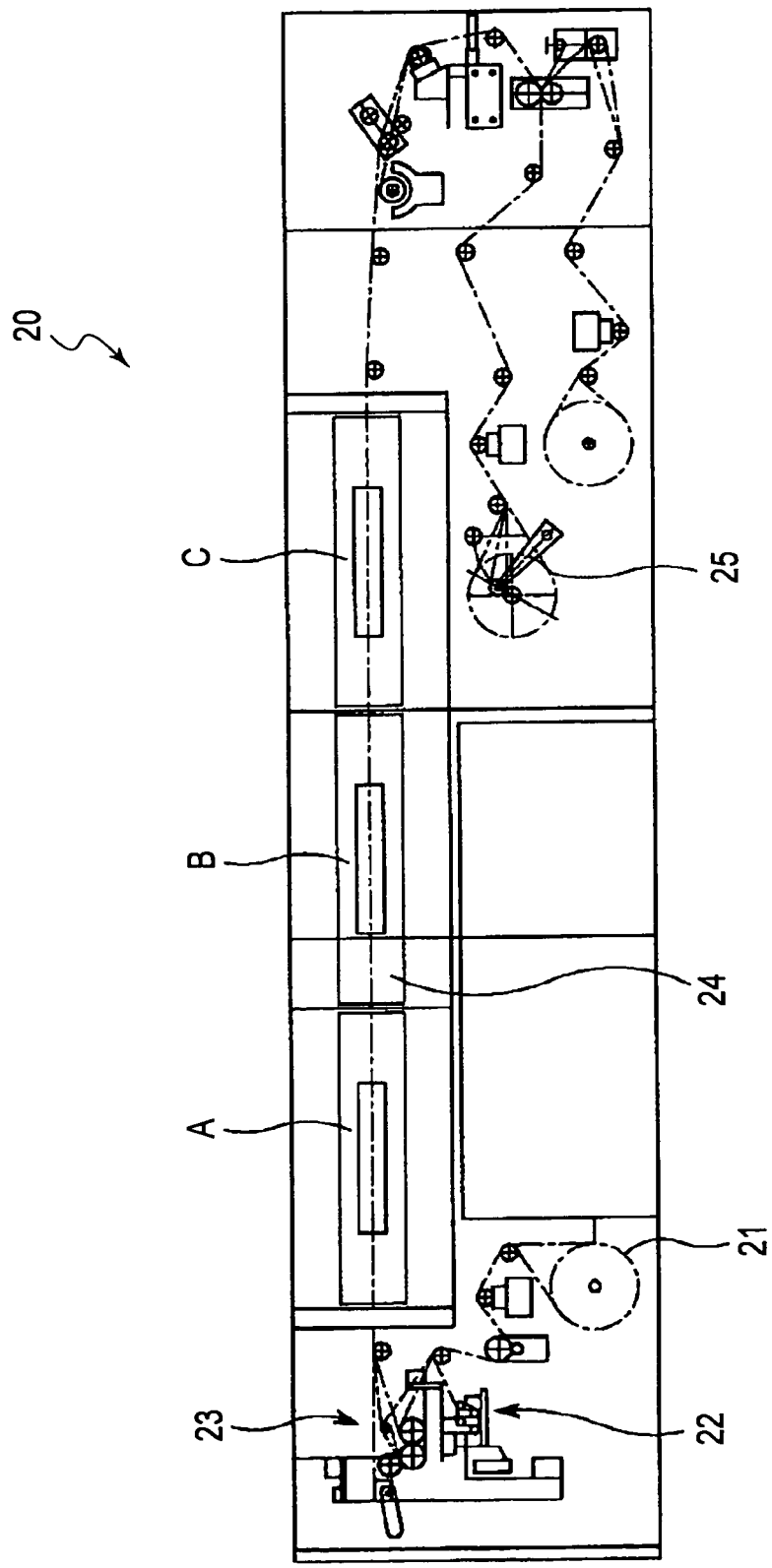
FIG. 2 is a view showing a multi-coater.

Referring to the drawings, specific embodiments to which the present invention is applied will be described below.

In this embodiment relating to a method for producing a functional material, included are: the steps of bringing a polyanion aqueous solution containing a functional component into contact with a base material (a sheet or a support body) to which a polyvalent metal cation aqueous solution (polyvalent metal salt aqueous solution) is attached and then drying the base material; or the steps of bringing a polyvalent metal salt aqueous solution into contact with the polyanion aqueous solution containing a functional component and then drying the base material. In other words, the functional material according to the present invention is produced by: utilizing a polyion complex method in which a gel is formed by ion-exchange between the polyanions and the cations in the polyvalent metal cation aqueous solution; and then drying the formed gel.

According to the present invention, polyvalent metal cations and polyanions are bonded to each other as described above to form an insoluble compound. During the formation process, the functional component is incorporated in the insoluble compound. In other words, the insoluble compound containing a desired functional component is formed on the surface of the obtained base material and fixed thereto.

The polyvalent metal cations in the insoluble compound are ion-exchanged with predetermined cations, which leads to redissolution of the insoluble compound. Thereby, the contained functional component can be released. Thus, the present invention can provide a functional material having excellent body fluid responsiveness.

The base material used in this embodiment is typified by a sheet such as a paper, a film, a fabric, a nonwoven fabric and the like. Here, the term "sheet" is not limited in any way in the width, length, and thickness, and is a concept including, for example, a film and a tape.

As the base material, other materials can be used such as point-bond, air-through, spunbond, thermal-bond, and spunlace nonwoven fabrics each formed of a hydrophobic fiber or a hydrophilic fiber, a stretchable nonwoven fabric, a water-disintegrable nonwoven fabric, a water-disintegrable paper, and a water-disintegrable film. The thermal-bond nonwoven fabric is particularly preferable because of its high strength and excellent workability.

The above-described stretchable fabric may be any one of: a fabric which is composed of fibers having crimps and thus has stretchability based on their deformation; a fabric which is formed by laminating nonwoven web layers, fiber web layers or film layers having extension properties, or a fabric which has a laminate of fibers made of elastomeric material as its all or part of the web composition.

The nonwoven web having an extension property refers to, for example, a web composed of a carded staple, a stretch-oriented spunbond web layer, and the like.

A fiber web having an extension property refers to one composed of a polyurethane-based, styrene block copolymer-based, olefin-based, or polyester-based elastomer.

The above-described water-disintegrable nonwoven fabric, water-disintegrable paper, and water-disintegrable film refer to all of those which can be disintegrated from a sheet form in a short time period when a large amount of water is supplied in a flush toilet or a sewage treatment tank, do not release harmful substances to microorganisms living in the sewage treatment tank and the sewage disposal plant, are disintegrated so as to have a fiber length of 20 nm or less if they are fabric materials, and do not rapidly increase BOD (Biochemical Oxygen Demand) if they are a water-soluble material.

In this embodiment, a sheet is used as the base material; however, the shape of the base material may be, for example, spherical or the like.

Examples of a solute in the aqueous solution containing polyvalent metal cations used in this embodiment include substances containing a calcium ion, a copper ion, an iron ion, an aluminum ion, a silver ion and the like. Specific examples of the solute include calcium chloride, calcium lactate, calcium gluconate, calcium nitrate, copper acetate, copper sulfate, iron sulfate, iron chloride, iron nitrate, aluminum chloride, aluminum sulfate, aluminum nitrate, silver nitrate, and the like. These polyvalent metal cations form insoluble compounds with the polyanions, and can be ion-exchanged with predetermined cations in the body fluid to redissolve the insoluble compound.

These may be used alone or in combination of multiple kinds.

In this embodiment, examples of the polyanion aqueous solution having ability to form a gel with the polyvalent metal cations include sodium alginate, gellan gum, carrageenan, hyaluronan, and the like. These substances are colloidal substances having extremely high viscosity and high hydrophilic nature, and easily dissolve in both cool and warm water.

These may be used alone or in combination of multiple kinds.

The concentration of the polyanion aqueous solution is preferably within a range of 0.05% by weight or more and less than 0.2% by weight in consideration of the film formation ability, the solubility and the viscosity. If the concentration is 0.2% by weight or more, a film is formed but the film tends to be difficult to redissolve in response to the body fluid. On the other hand, if the concentration is less than 0.05% by weight, no film may be formed.

The concentration of the polyvalent metal cations corresponding to the concentration of the polyanion aqueous solution is preferably within a range of 0.25% by weight to 0.5% by weight. If the concentration exceeds 0.5% by weight, it is difficult to prepare a functional film that is easily redissolves in response to the body fluid. On the other hand, if the concentration is less than 0.25% by weight, there is a risk because an alginate gel film is not formed.

Furthermore, a molar ratio of the sodium ions contained in the polyanion aqueous solution to the calcium ions contained in the polyvalent metal cation aqueous solution is preferably 1:5 to 1:10 from the viewpoint of film formation ability and the like.

The functional component used in this embodiment includes a moisture retention agent, an antibacterial agent, a deodorizing agent, an aroma agent, an anti-inflammatory agent and the like. These functional components may be used in combination of multiple kinds.

Examples of the moisture retention agent include ellagic acid, hydrolyzed collagen, sorbitol, trehalose, sodium hyaluronate, maltitol, mannitol silk fibroin, silk sericin, seaweed extracts, and the like.

Examples of the antibacterial agent include inorganic antibacterial agents such as silver-based, zinc-based and copper-based antibacterial agents; and organic antibacterial agents such as allyl isothiocyanates and catechins. These antibacterial agents exhibit excellent antibacterial effects against bacteria and fungi. In particular, the silver-based antibacterial agent is more preferable because a small amount thereof is needed to obtain a high antibacterial effect.

Examples of the deodorizing agent include green tea, bamboo extract, tannin, an abietic acid extract, a silk powder, a persimmon extract, flavonoid, catechin and the like.

The aroma agent is not particularly limited, as long as the aroma agent contains one or more kinds of aroma components selected from various kinds of natural aroma components and various kinds of synthesized aroma components. Specific examples of the aroma agent include: those from trees such as Japanese cypress and Japanese cedar, those from citruses such as lemon and bergamot, those from fruits such as strawberry and raspberry, those from flowering plants such as jasmine, lavender and rose, those from mints such as peppermint and spearmint, and further those releasing aroma, such as rush grass. Such an aroma agent may be an essential oil extracted from the roots, stem, branch, bark, flower petal, seed, or fruit of a plant by steam-distillation, expression, cold enfleurage, percolation, solvent extraction, or the like; alternatively, such an aroma agent may be a blend of aroma components isolated from essential oils or synthetic aroma components, such as monoterpene hydrocarbons, sesquiterpene hydrocarbons, monoterpene alcohols, sesquiterpene alcohols, phenols, aldehydes, ketones, esters, lactones, oxides and nitrogen-containing compounds.

Examples of the anti-inflammatory agent include extracts of peony, scutellaria root, hypericum, chamomile, a peach leaf, a Japanese medlar leaf, artemisia, Japanese basil, and the like.

The concentration of these functional components in the polyanion aqueous solution is not particularly limited and can be suitably determined in accordance with a targeted function. The concentration is generally preferably about 0.001 to 5% by weight, more preferably about 0.01 to 1% by weight.

The method in which the above-described polyvalent metal cation aqueous solution is brought into contact with the above-described base material is not particularly limited, as long as the method allows the polyvalent metal cations to be attached to the base material. For example, the contact of the polyvalent metal cation aqueous solution with the base material can preferably be achieved by coating the base material with the polyvalent metal cation aqueous solution or by immersing the base material in the polyvalent metal cation aqueous solution. Coating can be carried out by using a usual coating machine.

A method in which the polyanion aqueous solution is brought into contact with the base material which has been brought into contact with the polyvalent metal cation aqueous solution (that is, the base material including the polyvalent metal cations) is not particularly limited, as long as the method allows the component in the polyanion aqueous solution to be attached to the base material. As described above, the contact of the polyanion aqueous solution with the base material which has been brought into contact with the polyvalent metal cation aqueous solution can also be achieved by coating, immersion, or the like.

Likewise, in the case where the polyanion aqueous solution is first brought into contact with the base material and next the polyvalent metal cation aqueous solution is brought into contact, each of the liquids are brought into contact with the base material by the same method as described above.

Drying of the treated base material can be carried out for a predetermined time period and at a predetermined temperature by any method known to those skilled in the art.

The functional material thus obtained has a functional component-containing insoluble compound fixed thereto in which the polyvalent metal cations and the polyanions are bonded to each other. This results in exhibition of excellent body-fluid responsiveness of the functional material. For example, in a functional material responsive to sodium ions in the body fluid, calcium alginate formed by the bonding of calcium ions, which are the polyvalent metal cations, and the carboxylic groups of sodium alginate, which are the polyanions, to each other is fixed to the functional material. Here, the body fluid refers to a liquid obtained from a human being, an animal, a shellfish or a plant.

More specifically, the sodium ions and the calcium ions are ion-exchanged with each other to bond the carboxylic groups of the sodium alginate and the calcium ions to each other by electrostatic interaction. This allows insoluble calcium alginate having a cross-linking structure to be formed, resulting in the formation of a gel film on the surface of the sheet. At this time, the functional component is retained in the cross-linking structure. The following chemical formula (1) illustrates the cross-linking reaction of calcium alginate formed by the above-described electrostatic interaction.

[Chemical formula 1]

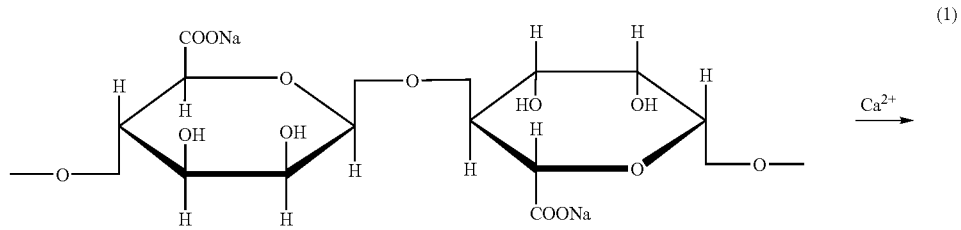

(1)

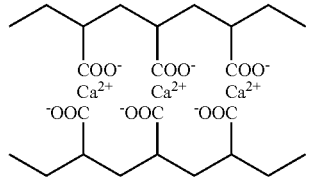

FIGS. 1(A) and (B) schematically show cross-sections of an obtained functional material produced in a way that first a polyvalent metal cation aqueous solution containing calcium ions as the polyvalent metal cations is brought into contact with a base material, and next a polyanion aqueous solution containing alginate anions as the polyanions is brought into contact with the base material. FIG. 1(B) is a schematic diagram of an enlarged cross-section of a part of FIG. 1(A).

A gel film 12 formed of alginate anions is stacked on a base material (sheet) 11 having calcium ions impregnated thereinto. This causes the cross-linking reaction shown in the above chemical formula (1) and results in the formation of a calcium alginate gel film. Specifically, as shown in FIG. 1(B), the calcium ions impregnated into the base material 11 and the alginate anions in the gel film 12 are cross-linked by electrostatic interaction. The calcium alginate gel film 12 thus obtained is dried to form a calcium alginate film capable of releasing the retained functional component therefrom upon contact with the body fluid such as sweat, urine, or the like.

When an aqueous solution containing sodium ions, such as sweat, urine, or the like is brought into contact with such a functional material, the insoluble calcium alginate is converted to soluble sodium alginate due to ion-exchange between calcium ions and sodium ions, and thereby redissolves. At this time, the destruction of the cross-linking structure results in the release of the functional component retained thereinside.

Next, an embodiment performed at a plant level, using a multi-coater (manufactured by HIRANO TECSEED Co., Ltd.) will then be described. This embodiment is conducted for a continuous and efficient production of functional sheets (a functional material). Detailed descriptions of the same contents as in the above-described embodiment are omitted.

Figure 3:
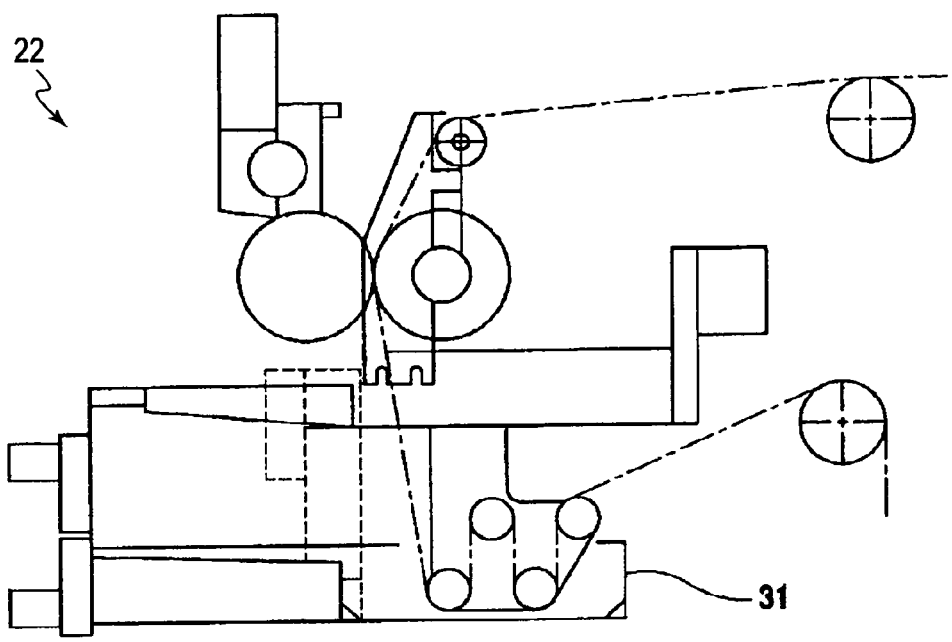
FIG. 3 is an enlarged view showing an impregnation coater in the multi-coater.
Figure 4:
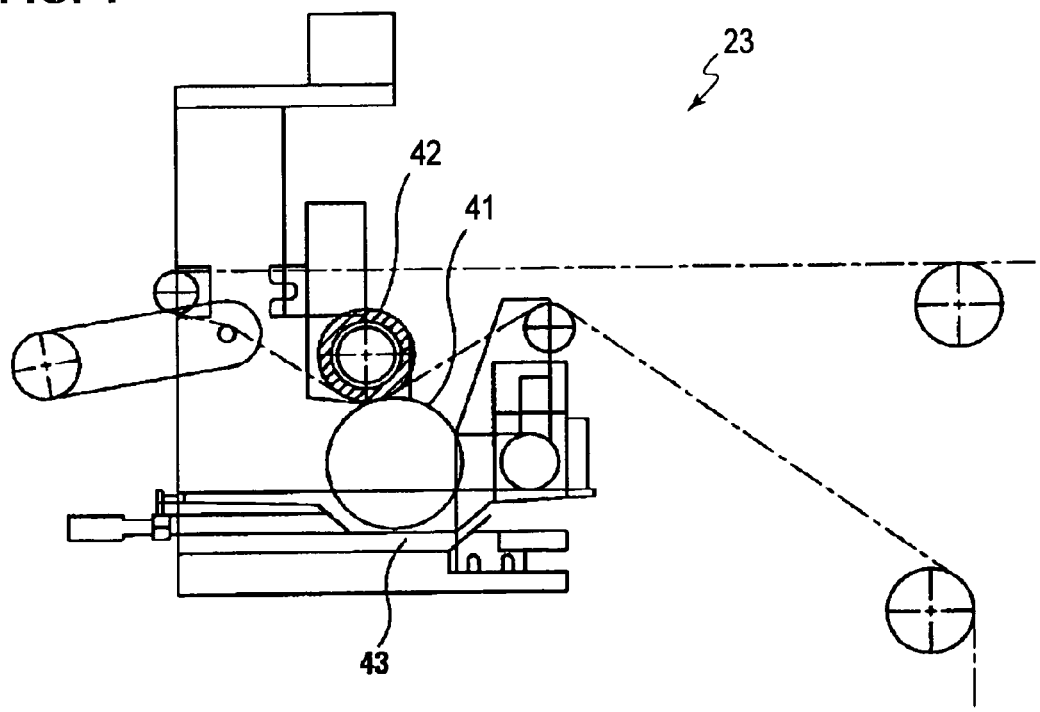
FIG. 4 is an enlarged view of a gravure coater in the multi-coater.

FIGS. 2 to 4 are layout drawings showing a multi-coater 20, an impregnation coater 22 and a gravure coater 23, respectively, which are used in this embodiment.

FIG. 2 is the layout drawing of the multi-coater 20, which is a machine for producing a sheet at a plant level. The multi-coater 20 includes: a first release unit 21 for continuously unrolling a sheet; an in-feed unit; a coating unit including the impregnation coater 22 and the gravure coater 23 for coating the sheet; a drying unit 24 for drying the sheet; an out-feed unit; and a wind-up unit 25 for winding up the coated sheet. The sheet serving as the base material is first transferred from the first release unit 21 to the in-feed unit, then through the coating unit to the drying unit 24, and finally through the out-feed unit to the wind-up unit 25. The impregnation coater 22 and the gravure coater 23 serving as the coating unit can be made compatible with various coating methods by rearranging parts such as a roll. The drying unit 24 has three chambers of driers A, B and C. Each of the chambers has a length of 1.5 m, resulting in the total length of the drying unit of 4.5 m. Note that, in Examples 7 and 8 and Reference Examples 10 and 11 to be described later, a machine additionally provided with a spray unit between the coating unit and the drying unit 24 is used.

FIG. 3 is the layout drawing of the impregnation coater 22 used in applying the polyvalent metal salt aqueous solution by an impregnation method. The polyvalent metal salt aqueous solution is put in the impregnation tank 31. The sheet is immersed in the impregnation tank 31 to attach the polyvalent, metal salt aqueous solution to the sheet.

FIG. 4 is the layout drawing of the gravure coater 23 used in applying the polyanion aqueous solution containing the functional component. The polyanion aqueous solution containing the functional component is put in a liquid tank 43. The polyanion aqueous solution is applied to a gravure roll 41. Then, the sheet is brought into contact with the gravure roll 41 to coat the sheet with the polyanion aqueous solution containing the functional component. This machine includes a back up roll 42 facing to the gravure roll 41.

In this embodiment, the functional sheet is produced by coating the sheet with the polyvalent metal salt aqueous solution using the impregnation coater 22 by an impregnation method, and coating again the sheet with the polyanion aqueous solution containing the functional component such as a moisture retention agent using the gravure coater 23 by a gravure roll method. Alternatively, the functional sheet is produced by applying the polyanion aqueous solution containing the functional component such as a moisture retention agent using the gravure coater 23 by a gravure roll method, and then spraying the polyvalent metal salt aqueous solution to the sheet using the spray unit.

In addition to the gravure roll method, the method for coating the base material (support body) with the polyanion aqueous solution containing the functional component such as a moisture retention agent can be appropriately selected from known methods including an impregnation method, a mayer bar method, a roll method, a gravure roll method, a reverse roll method, a blade method, a knife method, an air knife method, an extrusion method, a cast method, a rotary screen method and the like.

In this embodiment, a dot pattern coating by using a coating method such as a rotary screen method makes it possible to distribute required amounts of the functional component to required places. As compared with uniform coating on an entire surface of the base material sheet, the patterned coating is more efficient, thus suppresses the increase in cost, makes it possible to place different kinds of functional components on different coating places, and can prevent the deterioration of feel and skin touch caused by resin coating. The patterned coating can prevent the deterioration of the absorbing property for the use as a surface material of a disposable diaper, while the entire surface coating causes the alginate resin to form a coating film, resulting in the deterioration of a moisture-absorption property.

The sheet-like structure including the functional material obtained in the above manner can be used in various kinds of applications such as packing materials for foods, a kitchen paper and a medical-use sheet. The configuration of the sheet-like structure is not particularly limited, as long as the sheet-like structure includes the above-described sheet-like functional material. If needed, the structure may be provided with any layer, for example, a water-repellent layer, a bonding layer, an adhesion layer, and the like; alternatively, another sheet-like base material may further be stacked on the structure.

In addition, examples of sanitary products to which the functional material or sheet-like structure obtained in the above manner is applied include: absorbent products such as a disposable diaper, a sanitary napkin, a panty liner and a urine pad; a wound protection sheet; and a wipe for human body. The specific configuration is not particularly limited, as long as the configuration includes the above-described functional material.

Next, specific examples of the present invention will be described. It is clear that the present invention is not limited by the insignificant details of the test conditions employed in the Examples shown below in consideration of the common sense regarding research in this field.

EXAMPLE 1

In Example 1, polypropylene was used as a main fiber. An air-through thermal-bond nonwoven fabric (manufactured by Unicharm Corporation) having a thickness of 2.0 mm, a weight per unit area of 29 g/m² and a material width of 350 mm was immersed in a 0.25% by weight calcium chloride (manufactured by Wako Pure Chemical Industries, Ltd.) aqueous solution for one second. Thereafter, this synthetic nonwoven fabric was immersed in a 0.05% by weight sodium alginate (manufactured by Wako Pure Chemical Industries, Ltd.) aqueous solution containing 0.5% by weight of ellagic acid (manufactured by Wako Pure Chemical Industries, Ltd.) for about five minutes. Thereafter, this synthetic nonwoven fabric was dried in a drier at 105° C. for 30 minutes to obtain a functional sheet (functional film).

EXAMPLES 2 TO 4

In Example 2, the same processes as in Example 1 were performed except that the concentration of the calcium chloride aqueous solution was changed to 0.5% by weight.

In Example 3, the same processes as in Example 1 were performed except that the concentration of the sodium alginate aqueous solution containing 0.5% by weight of ellagic acid was changed to 0.1% by weight.

In Example 4, the same processes as in Example 1 were performed except that the concentration of the calcium chloride aqueous solution was changed to 0.5% by weight and the concentration of the sodium alginate aqueous solution containing 0.5% by weight of ellagic acid was changed to 0.1% by weight.

REFERENCE EXAMPLES 1 TO 8

In Reference Example 1, the same processes as in Example 1 were performed except that the concentration of the sodium alginate aqueous solution containing 0.5% by weight of ellagic acid was changed to 0.5% by weight.

In Reference Example 2, the same processes as in Example 2 were performed except that the concentration of the sodium alginate aqueous solution containing 0.5% by weight of ellagic acid was changed to 0.5% by weight.

In Reference Example 3, the same processes as in Example 3 were performed except that a calcium chloride aqueous solution was not added.

In Reference Example 4, the same processes as in Example 1 were performed except that the concentration of the calcium chloride aqueous solution was changed to 1% by weight.

In Reference Example 5, the same processes as in Example 3 were performed except that the concentration of the calcium chloride aqueous solution was changed to 1% by weight.

In Reference Example 6, the same processes as in Example 1 were performed except that the concentration of the sodium alginate aqueous solution containing 0.5% by weight of ellagic acid was changed to 0.2% by weight.

In Reference Example 7, the same processes as in Example 1 were performed except that the concentration of the calcium chloride aqueous solution was changed to 0.5% by weight and the concentration of the sodium alginate aqueous solution containing 0.5% by weight of ellagic acid was changed to 0.2% by weight.

In Reference Example 8, the same processes as in Example 1 were performed except that the concentration of the calcium chloride aqueous solution was changed to 1.0% by weight and the concentration of the sodium alginate aqueous solution containing 0.5% by weight of ellagic acid was changed to 0.2% by weight.

<Function Evaluation 1>

Function evaluation of the functional sheets manufactured in the above described Examples 1 to 4 and Reference examples 1 to 8 was carried out as follows.

First, the prepared sheet (1 cm×1 cm) was immersed in 2 ml of 0.65% by weight sodium chloride (manufactured by Wako Pure Chemical Industries, Ltd.) aqueous solution or pure water (prepared with an automatic water distillation apparatus RFD250NA (manufactured by Advantec Toyo Kaisha, Ltd.)) for 30 minutes to carry out an elution test of ellagic acid. Thereafter, the solvent was completely evaporated. Then, the remaining ellagic acid was dissolved in 3 ml of 0.01 M sodium hydroxide (manufactured by Wako Pure Chemical Industries, Ltd.) aqueous solution. Subsequently, measurement was performed with a high speed liquid chromatograph (manufactured by Shimadzu Corporation). The evaluation was made while the amount of ellagic acid eluted when a sheet (1 cm×1 cm) was immersed in 5 ml of 0.01 M NaOH was taken as the amount of fixed ellagic acid.

The eluted amount was calculated as follows:

Elution ratio (%)=(amount of eluted ellagic acid/amount of fixed ellagic acid)×100

Table 1 below shows the results of examples 1 to 4 and Reference Examples 1 to 8.

TABLE 1

|  | Amount of fixed ellagic acid (µg/cm²) | Amount of eluted ellagic acid (µg/cm²) | | Elution ratio (%) | |
| --- | --- | --- | --- | --- | --- |
|  |  | NaCl | Pure water | NaCl | Pure water |
| Example 1 | 389.7 | 43.28 | 2.543 | 11.1 | 0.65 |
| Example 2 | 410.1 | 397.7 | 5.320 | 97.0 | 1.30 |
| Example 3 | 420.0 | 141.7 | 6.049 | 33.75 | 1.44 |
| Example 4 | 574.5 | 483.5 | 0.583 | 84.17 | 0.10 |
| Reference Example 1 | 204.8 | 0.606 | 4.682 | 0.30 | 2.29 |
| Reference Example 2 | 259.1 | 0.010 | 1.152 | 0.004 | 0.44 |
| Reference Example 3 | 2.98 | 0.048 | 0.208 | 1.611 | 6.98 |
| Reference Example 4 | 682.2 | 7.300 | 0.255 | 1.07 | 0.04 |

TABLE 1-continued

|  | Amount of fixed ellagic acid ($\mu g/cm^2$) | Amount of eluted ellagic acid ($\mu g/cm^2$) | | Elution ratio (%) | |
| --- | --- | --- | --- | --- | --- |
|  |  | NaCl | Pure water | NaCl | Pure water |
| Reference Example 5 | 813.8 | 39.24 | 0.601 | 4.8 | 0.073 |
| Reference Example 6 | 363.6 | 7.00 | 2.14 | 1.93 | 0.589 |
| Reference Example 7 | 383.4 | 0.155 | 0.227 | 0.040 | 0.059 |
| Reference Example 8 | 657.0 | 0.477 | 0.240 | 0.0726 | 0.037 |

As seen in Table 1, in each of Examples 1 to 4, ellagic acid was sufficiently fixed, and when the sheet was immersed in a sodium chloride aqueous solution, a satisfactory eluted amount and elution ratio of ellagic acid were obtained.

In Reference Example 1, the elution ratio of ellagic acid was low because the concentration of the sodium alginate aqueous solution was as high as 0.5% by weight.

In Reference Example 2, the elution ratio of ellagic acid was low because both the concentration of the sodium alginate aqueous solution and the concentration of the calcium chloride aqueous solution were as high as 0.5% by weight.

In Reference Example 3, both the fixed amount of ellagic acid and the elution ratio of ellagic acid were low because the calcium chloride aqueous solution was not added.

In Reference Example 4, the fixed amount of ellagic acid was high but the elution ratio of ellagic acid was low because the concentration of the calcium chloride aqueous solution was as high as 1% by weight, although the concentration of the sodium alginate aqueous solution was 0.05% by weight.

In Reference Example 5, the fixed amount of ellagic acid was high but the elution ratio of ellagic acid was low because the concentration of the calcium chloride aqueous solution was as high as 1% by weight, although the concentration of the sodium alginate aqueous solution was 0.1% by weight.

In Reference Example 6, the fixed amount of ellagic acid was high but the elution ratio of ellagic acid was low because the concentration of the sodium alginate aqueous solution was as high as 0.2% by weight, although the concentration of calcium chloride was 0.25% by weight.

In Reference Example 7, the fixed amount of ellagic acid was high but the elution ratio of ellagic acid was low because the concentration of calcium chloride was as high as 0.5% by weight and because the concentration of the sodium alginate aqueous solution was as high as 0.2% by weight.

In Reference Example 8, the fixed amount of ellagic acid was high but the elution ratio of ellagic acid was low because the concentration of calcium chloride was 1% by weight and the concentration of the sodium alginate aqueous solution was as high as 0.2% by weight.

Examples and Reference Examples below were conducted by using the equipment shown in FIGS. 2 to 4.

EXAMPLE 5

In Example 5, a synthetic nonwoven fabric was first coated with 0.5% by weight calcium lactate (manufactured by KANTO CHEMICAL CO., INC.) aqueous solution at 0.72 $g/m^2$, using the impregnation coater 22, by an impregnation method. Then, this synthetic nonwoven fabric was coated with 0.1% by weight sodium alginate aqueous solution containing 0.5% by weight of ellagic acid with the gravure coater 23. The gravure roll used was of an oblique type and had a number of lines of 50 and a depth of 200 μm. Subsequently, the synthetic nonwoven fabric was dried. Here, the coating speed was 2.0 m/min, and the drying temperatures of the drying equipment 24 shown in FIG. 2 were 90° C. in drying chambers A and B and 100° C. in drying chamber C. The gravure roll 41 used was of an oblique type and had a number of lines of 50 and a depth of 200 μm.

Figure 5:
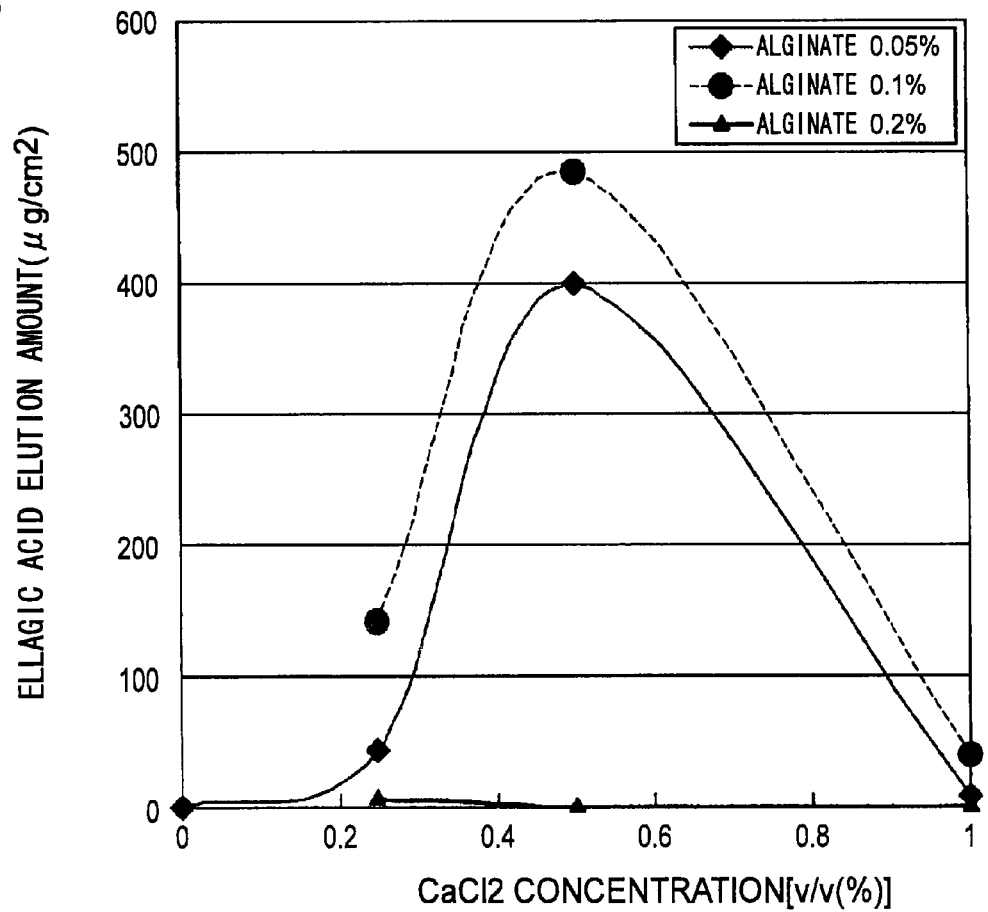
FIG. 5 is a graph showing the results of the amount of ellagic acid eluted from a functional sheet in Function Evaluation 1.

Note that this Example was performed with reference to the conditions of Example 4, which resulted in the largest elution amount of ellagic acid of 483.5 $\mu g/cm^2$, a high elution ratio in the sodium chloride aqueous solution, and the lowest elution ratio in water, as shown in FIG. 5.

EXAMPLE 6

In Example 6, the processes were performed in the same manner as in Example 5 except that the calcium lactate aqueous solution was applied so as to be 0.35 $g/m^2$.

EXAMPLE 7

In Example 7, a synthetic nonwoven fabric was gravure-coated (#50) with 0.1% by weight sodium alginate aqueous solution containing 0.5% by weight of ellagic acid, by using the gravure coater 23. Thereafter, 0.5% by weight calcium lactate aqueous solution was sprayed to the synthetic nonwoven fabric so as to be 1.03 $g/m^2$, by using a spray. Then, the synthetic nonwoven fabric was dried. Note that the coating speed was 2.0 m/min, and the temperatures of the drying equipment 24 were 90° C. in the drying chambers A and B and 100° C. in the drying chamber C.

EXAMPLE 8

In Example 8, the processes were performed in the same manner as in Example 7 except that 0.2% by weight sodium alginate aqueous solution containing 0.5% by weight of ellagic acid was used.

REFERENCE EXAMPLES 9 TO 11

In Reference Example 9, the processes were performed in the same manner as in Example 6 except that the calcium chloride aqueous solution was used in place of the calcium lactate aqueous solution.

In Reference Example 10, the processes were performed in the same manner as in Example 7 except that the calcium chloride aqueous solution was used in place of the calcium lactate aqueous solution, and 1% by weight sodium alginate aqueous solution containing 0.5% by weight of ellagic acid was used.

In Reference Example 11, the processes were performed in the same manner as in Example 7 except that 1% by weight calcium chloride aqueous solution was used in place of 0.5% by weight calcium lactate aqueous solution, and 1% by weight sodium alginate aqueous solution containing 0.5% by weight of ellagic acid was used.

<Function Evaluation 2>

Function evaluation of the functional sheet manufactured in each of Examples 5 to 8 and Reference Examples 9 to 11 was carried out as follows.

First, a prepared sheet (3 cm×3 cm) was immersed in 3 ml of 0.65% by weight sodium chloride aqueous solution or pure water for 30 minutes to carry out an elution test of ellagic acid. Thereafter, the solvent was completely evaporated. Then, the remaining ellagic acid was dissolved in 3 ml of 0.01 M sodium hydroxide aqueous solution. Subsequently, measurement was performed with a high speed liquid chromatograph. Note that the evaluation was made while the amount of ellagic acid eluted when a sheet (1 cm×1 cm) was immersed in 5 ml of 0.01 M NaOH aqueous solution was taken as the amount of fixed ellagic acid.

Table 2 below shows the results of examples 5 to 8 and Reference Examples 9 to 11.

TABLE 2

|  | Amount of fixed ellagic acid ($\mu g/cm^2$) | Amount of eluted ellagic acid ($\mu g/cm^2$) | | Elution ratio (%) | |
| --- | --- | --- | --- | --- | --- |
|  |  | NaCl | Pure water | NaCl | Pure water |
| Example 5 | 0.102 | 0.033 | 0.027 | 32.4 | 26.4 |
| Example 6 | 0.136 | 0.051 | 0.042 | 37.5 | 30.9 |
| Example 7 | 0.370 | 0.091 | 0.062 | 24.6 | 16.8 |
| Example 8 | 0.193 | 0.059 | 0.036 | 30.6 | 18.7 |
| Reference Example 9 | Not fixed | — | — | — | — |
| Reference Example 10 | 0.046 | 0.018 | 0.038 | 39.1 | 82.6 |
| Reference Example 11 | 0.083 | 0 | 0.074 | 0 | 89.2 |

As seen in Table 2, in each of Examples 5 to 8, ellagic acid was sufficiently fixed, and when the sheet was immersed in a sodium chloride aqueous solution, a satisfactory eluted amount and elution ratio of ellagic acid were obtained.

In Example 9, the calcium chloride aqueous solution was used in place of the calcium lactate aqueous solution. Consequently, ellagic acid was not fixed to the sheet. This was because calcium chloride gelatinized sodium alginate at a higher gelatinization speed than calcium lactate so that sodium alginate was gelatinized in the liquid tank. In other words, calcium chloride and sodium alginate reacted with each other in the liquid tank of the gravure coater 23.

In Reference Example 10, the calcium chloride aqueous solution was used in place of an emulsified calcium aqueous solution, and the concentration of sodium alginate was changed to 1% by weight. Consequently, the fixation of ellagic acid was slightly observed. However, the selectivity to the sodium chloride aqueous solution in elution of ellagic acid was low.

In Reference Example 11, the concentration of calcium chloride was changed to 1% by weight. Consequently, ellagic acid was not eluted in the sodium chloride aqueous solution.

As described above, in Examples performed at a plant level, according to this embodiment, the elution ratios of ellagic acid in the cases of immersion in the sodium chloride aqueous solution were high, as compared with the cases of immersion in pure water. In other words, it can be said that calcium alginate formed on the sheet surface had sodium ion selectivity, and was ion-exchanged with sodium ions contained in the body fluid and the like to dissolve and release ellagic acid.

The invention claimed is:

1. A method for producing a functional material, comprising the steps of:
   bringing a polyvalent metal cation aqueous solution into contact with a base material;
   bringing a polyanion aqueous solution containing a functional component into contact with the base material previously in contact with the polyvalent metal cation aqueous solution to bond the polyvalent metal cations and the polyanions to each other, and thereby forming an insoluble compound containing a functional component; and
   drying the base material including the insoluble compound, wherein
   the polyanion aqueous solution includes sodium alginate,
   a concentration of the polyanion aqueous solution is from 0.05% by weight or more to less than 0.2% by weight,
   a concentration of the polyvalent metal cation aqueous solution is within a range of 0.25% by weight to 0.5% by weight, and
   a molar ratio of the sodium ions contained in the polyanion aqueous solution to the sodium ions contained in the polyvalent metal cation aqueous solution is 1:5 to 1:10.

2. The method for producing a functional material according to claim 1, wherein the polyvalent metal cation aqueous solution contains calcium ions, and the polyanion aqueous solution contains sodium alginate.

3. The method for producing a functional material according to claim 2, wherein a molar ratio of sodium ions contained in the polyanion aqueous solution to calcium ions contained in the polyvalent metal cation aqueous solution is 1:5 to 1:10.

* * * * *

UNITED STATES PATENT AND TRADEMARK OFFICE
CERTIFICATE OF CORRECTION

PATENT NO. : 8,440,731 B2  
APPLICATION NO. : 12/449087  
DATED : May 14, 2013  
INVENTOR(S) : Ichiura et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 856 days.

Signed and Sealed this
Eighth Day of September, 2015

Michelle K. Lee
*Director of the United States Patent and Trademark Office*